(12) United States Patent
Vecchini et al.

(10) Patent No.: US 10,173,947 B2
(45) Date of Patent: Jan. 8, 2019

(54) PROCESS FOR THE PRODUCTION OF 1,3-BUTADIENE FROM 1,3-BUTANEDIOL

(71) Applicant: Versalis S.p.A., San Donato Milanese (IT)

(72) Inventors: Nicola Vecchini, Verona (IT); Armando Galeotti, Gonzaga (IT); Andrea Pisano, Mantova (IT)

(73) Assignee: Versalis S.p.A., San Donato Milanese (IT)

( * ) Notice: Subject to any disclaimer, the term of this patent is extended or adjusted under 35 U.S.C. 154(b) by 6 days.

(21) Appl. No.: 15/529,778

(22) PCT Filed: Dec. 11, 2015

(86) PCT No.: PCT/EP2015/079378
§ 371 (c)(1),
(2) Date: May 25, 2017

(87) PCT Pub. No.: WO2016/092063
PCT Pub. Date: Jun. 16, 2016

(65) Prior Publication Data
US 2017/0313633 A1 Nov. 2, 2017

(30) Foreign Application Priority Data

Dec. 12, 2014 (IT) .............................. MI2014A2121

(51) Int. Cl.
*C07C 1/24* (2006.01)
*C07C 29/60* (2006.01)
*C12P 7/18* (2006.01)

(52) U.S. Cl.
CPC ............... *C07C 1/24* (2013.01); *C07C 29/60* (2013.01); *C12P 7/18* (2013.01)

(58) Field of Classification Search
CPC ......... C07C 29/60; C07C 1/24; C07C 11/167; C07C 33/025; C07C 33/03; C12P 7/18
See application file for complete search history.

(56) References Cited

U.S. PATENT DOCUMENTS

| | | | |
|---|---|---|---|
| 2,174,280 A | 9/1939 | Wellman et al. | |
| 2,310,809 A | 2/1943 | Reppe et al. | |
| 2,373,153 A | 4/1945 | Tollefson et al. | |
| 2,426,678 A | 9/1947 | Greenberg | |
| 4,400,562 A | 8/1983 | Wagaman et al. | |
| 5,406,007 A | 4/1995 | Falling et al. | |
| 2010/0330635 A1 | 12/2010 | Burgard et al. | |
| 2011/0000335 A1 | 1/2011 | Lixiang | |
| 2012/0329113 A1* | 12/2012 | Burgard | C12N 15/52 435/158 |
| 2013/0066035 A1 | 3/2013 | Burgard et al. | |
| 2013/0109064 A1 | 5/2013 | Osterhout et al. | |

FOREIGN PATENT DOCUMENTS

| | | |
|---|---|---|
| DE | 1150671 B | 6/1963 |
| DE | 1908620 A1 | 9/1970 |
| IT | MI2013A002069 A1 | 6/2015 |
| JP | 63/222135 | 9/1998 |
| SU | 396312 A1 | 8/1973 |
| WO | WO2014118484 A1 | 8/2014 |

OTHER PUBLICATIONS

International Search Report for PCT/EP2015/079378 dated Feb. 17, 2016, 13 pages.
Sato et al, "Dehydration of Diols Catalyzed by CeO2," Journal of Molecular Catalysis, vol. 221, Published Nov. 2004, pp. 177-183.
Takashi et al, "Vapor-Phase Dehydration of 1,3-butanediol over CeO2—ZrO2 Catalysts," Topics in Catalysis, Kluwer Academic Publishers-Plenum Publishers, vol. 52, published Apr. 2009, pp. 609-617.
Gräfje H. et al. in "Butanediols, Butenediol, and Butynediol", "Ulmann's Encyclopedia of Industrial Chemistry" (2000).
"Merck Index" (1976), 9th Edition.
Winfield M. E. in "The catalytic dehydration of 2,3-butanediol to butadiene. II. Adsorption Equilibria", "Australian Journal of Scientific Research" (1950), vol. 3(2), pp. 290-305.

(Continued)

*Primary Examiner* — Sharon Pregler
(74) *Attorney, Agent, or Firm* — Abel Law Group, LLP

(57) ABSTRACT

Process for the production of 1,3-butadiene comprising: feeding a mixture (a) comprising 1,3-butanediol and water to an evaporator, said water being present in an amount of greater than or equal to 5% by weight, preferably ranging from 10% by weight to 85% by weight, more preferably ranging from 15% by weight to 30% by weight, relative to the total weight of said mixture (a), to obtain: (b) a gaseous stream comprising 1,3-butanediol exiting from the top of said evaporator; and, optionally, (c) a blowdown stream exiting from the bottom of said evaporator; feeding said gaseous stream (b) to a first reactor containing at least one dehydration catalyst to obtain (d) a stream comprising alkenols, water and, optionally, impurities and/or unreacted 1,3-butanediol, exiting from said first reactor; optionally, feeding said stream (d) to a first purification section to obtain: (e) a stream comprising alkenols, water, and, optionally, impurities; (f) a stream comprising water and, optionally, impurities and/or unreacted, 3-butanediol; and, optionally, (f) a stream comprising impurities; feeding said stream (d) or said stream (e) to a second reactor containing at least one dehydration catalyst to obtain (g) a stream comprising 1,3-butadiene, water and, optionally, impurities and/or unreacted alkenols, exiting from said second reactor; feeding said stream (g) to a second purification section to obtain: (h) a stream comprising pure 1,3-butadiene; (i) a stream comprising water and, optionally, unreacted alkenols; and, optionally, (1) a stream comprising impurities. Said 1,3-butadiene may advantageously be used as a monomer or intermediate in the production of elastomers and (co)polymers.

26 Claims, 1 Drawing Sheet

(56) References Cited

OTHER PUBLICATIONS

Sato S. et al., in "Catalysis Communications" (2003), vol. 4, pp. 77-81.
Sato S. et al., in "Catalysis Communications" (2004), vol. 5, pp. 397-400.
Sato S. et al., in "Applied Catalysis A: General" (2007),vol. 328, pp. 109-116.
Gotoh H. et al., in "Applied Catalysis A: General" (2010), vol. 377, pp. 92-98.
Hichikawa N. et al., in "Journal of Molecular Catalysis A: Chemical" (2006), vol. 256, pp. 106-112.
"Process Heat Transfer", Donald Q. Kern, McGraw-Hill (1950), Chapter 14, Evaporator, pp. 375-510.
Perry's Chemical Engineers' Handbook, McGraw-Hill (7th Ed.—1997), Section 11, pp. 108-118.

* cited by examiner

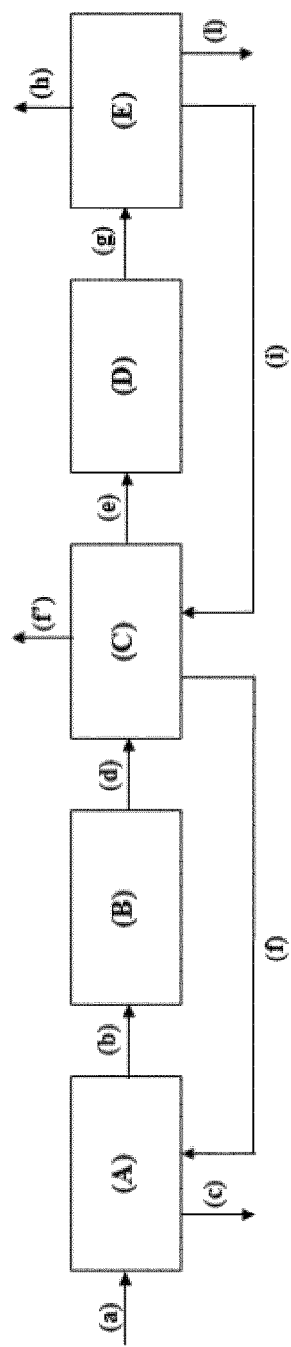

PROCESS FOR THE PRODUCTION OF 1,3-BUTADIENE FROM 1,3-BUTANEDIOL

The present invention relates to a process for the production of 1,3-butadiene from 1,3-butanediol.

More particularly, the present invention relates to a process for the production of 1,3-butadiene comprising feeding a mixture comprising 1,3-butanediol and water to an evaporator, said water being present in an amount of greater than or equal to 5% by weight relative to the total weight of said mixture; feeding the gaseous stream comprising 1,3-butanediol exiting from the top of said evaporator to a first reactor containing at least one dehydration catalyst; optionally feeding the stream comprising alkenols, water and, optionally, impurities and/or unreacted 1,3-butanediol, exiting from said first reactor to a purification section; feeding the, optionally purified, stream comprising alkenols, water and, optionally, impurities and/or unreacted 1,3-butanediol, to a second reactor containing at least one dehydration catalyst to obtain a stream comprising 1,3-butadiene, water and, optionally, impurities and/or unreacted alkenols; recovering the 1,3-butadiene from said stream. Preferably, said mixture comprising 1,3-butanediol and water is derived from the fermentation of sugars obtained from biomass.

Said 1,3-butadiene may advantageously be used as a monomer or intermediate in the production of elastomers and (co)polymers.

It should also be noted that the alkenols obtained from the above-stated process, i.e. from the dehydration of 1,3-butanediol in the first reactor, namely 2-buten-1-ol (crotyl alcohol), 3-buten-2-ol (methyl vinyl carbinol), 3-buten-1-ol (allyl carbinol), more particularly 2-buten-1-ol (crotyl alcohol) and 3-buten-2-ol (methyl vinyl carbinol), may advantageously be used, other than for the production of 1,3-butadiene, in the production of intermediates which are in turn usable in fine chemistry, agricultural chemistry, pharmaceutical chemistry, or in petrochemistry.

For the aim of the present description and the following claims, the term 2-buten-1-ol (crotyl alcohol) is taken to mean: either a mixture of the cis and trans isomers, or the cis isomer as such, or the trans isomer as such.

2-Buten-1-ol (crotyl alcohol) may, for example, be used as a precursor for halides, crotyl esters, or crotyl ethers which, in turn, may be used, for example, as intermediates in the production of monomers (for example, for the production of sorbic acid, trimethylhydroquinone, crotonic acid, 3-methoxybutanol), in agricultural chemistry, in pharmaceutical chemistry.

3-Buten-2-ol (methyl vinyl carbinol) may be used as a solvent, in fine chemistry, as a component in the modification of polymers such as, for example, polyolefins (as described, for example, in German patent DE 1,908,620).

3-Buten-1-ol (allyl carbinol) may be used, for example, as a raw material in pharmaceutical chemistry, in agricultural chemistry, in perfumes, in resins. For example, aryl-substituted aldehydes which may be used in pharmaceutical chemistry, for example, as folic acid antagonists, may be obtained from the coupling reaction of 3-buten-1-ol (allyl carbinol) with aryl halides, catalysed by palladium.

It is known that, at present, industrial production of 1,3-butanediol, 1,3-butadiene and alkenols is based on conventional petrochemical processes.

The reason for this is that, since diols in general, and 1,3-butanediol (generally also denoted as 1,3-BDO) in particular, have four carbon atoms, they are generally obtained by means of complex petrochemical processes as described, for example by Grafje H. et al. in "Butanediols, Butenediol, and Butynediol", *"Ulmann's Encyclopedia of Industrial Chemistry"* (2000). In particular, 1,3-butanediol is produced via acetaldehyde, hydroxybutyraldehyde and subsequent reduction, and is generally used as a component of resins or as a solvent.

American U.S. Pat. No. 5,406,007 describes a process for the preparation of an allylic alcohol, a homoallylic alcohol, or a mixture thereof, comprising hydrogenating an epoxyalkene, in which the epoxy group and ethylenic unsaturation are conjugated in the presence of a sulfur-modified or sulfided nickel catalyst under conditions of temperature and of pressure typical of hydrogenation. Preferably, said process is useful for the preparation of a mixture of 2-buten-1-ol (crotyl alcohol) and 3-buten-1-ol (allyl carbinol). American U.S. Pat. No. 6,278,031 describes a process for the preparation of 2-buten-1-ol compounds having the formula (I):

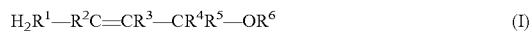

$$H_2R^1—R^2C=CR^3—CR^4R^5—OR^6 \quad (I)$$

in which the $R^1$, $R^2$, $R^3$, $R^4$, $R^5$ and $R^6$ radicals are, mutually independently, hydrogen or an aliphatic radical optionally substituted with an OH, or with a group OR in which R is an aliphatic group, a halogen or a carboxyl group, furthermore $R^2$ represents a —CHO radical, or $R^2$ and $R^5$ together with the carbon atoms located therebetween form an alicyclic ring, and $R^6$ additionally represents a cycloaliphatic, araliphatic, aromatic radical or a radical —C(=O)—$R^7$ in which $R^7$ is an aliphatic, cycloaliphatic, araliphatic or aromatic radical, said process comprising isomerising 3-buten-1-ol compounds having the formula (II):

$$HR^1C=CR^2—CHR^3—CR^4R^5—OR^6 \quad (II)$$

in which the $R^1$, $R^2$, $R^3$, $R^4$, $R^5$ and $R^6$ radicals, have the same meanings described above, in the presence of hydrogen and of a catalyst, in which the process is carried out continuously on a fixed-bed catalyst, in which the catalyst comprises palladium and selenium or tellurium or a mixture of selenium and tellurium on a silicon dioxide support, and has a BET surface area ranging from 80 m²/g to 380 m²/g and a pore volume ranging from 0.6 cm³/g to 0.95 cm³/g in a pore diameter ranging from 3 nm to 300 μm, with from 80% to 95% of the pore volume being in a pore diameter ranging from 10 nm to 100 nm. Alternatively, 2-buten-1-ol (crotyl alcohol) may be prepared by reduction of crotonaldehyde as described, for example, in "Merck Index" (1976), 9th Edition.

American U.S. Pat. No. 4,400,562 describes a method for synthesising an alkenol from 1,3-butanediol in the liquid phase comprising: mixing a sulfate of a trivalent metal selected from aluminium sulfate, chromium sulphate, iron sulfate, and mixtures thereof, as catalyst, with 1,3-butanediol, in an effective quantity to obtain a mixture of said catalyst suspended in 1,3-butanediol; heating said mixture to a temperature of about 70° C. below to about 100° C. below the boiling point of 1,3-butanediol, to obtain partial dehydration of 1,3-butanediol to 3-buten-1-ol which evaporates from the reaction mixture; and condensing said vapour so as to isolate the 3-buten-1-ol.

3-Buten-2-ol (methyl vinyl carbinol) and butadiene may be obtained by dehydration of 2,3-butanediol in the presence of thorium oxide as described, for example, by Winfield M. E. in "The catalytic dehydration of 2,3-butanediol to butadiene. II. Adsorption Equilibria", *"Australian Journal of Scientific Research"* (1950), Vol. 3(2), pp. 290-305.

Alternatively, 3-buten-2-ol (methyl vinyl carbinol), alone or in a mixture with other butenols, may be obtained for example: by thermal decomposition of polyols or the derivatives thereof (for example, 1,3-butylene glycol diacetate) as described, for example, in German patent DE 1,150,671; or by reduction of acetylenes or of unsaturated carbonyl compounds as described, for example, in Russian patent SU 396312 or in Japanese patent application JP 63/222135.

The possibility of developing alternative production processes for alkenols and 1,3-butadiene which are efficient, have higher productivity, lower production costs and reduced environmental impact, remains of great interest. In particular, new processes capable of using materials derived from biosynthetic processes, for example 1,3-butanediol derived from renewable sources such as, for example, biomass (i.e. bio-1,3-butanediol), to yield, by catalytic dehydration, bio-alkenols which may in turn be used for the production of bio-1,3-butadiene, are certainly of interest.

Processes for the dehydration of diols and butanediols to alkenols in the presence of catalysts, in particular catalysts based on cerium oxide, are known in the art.

For example, Sato S. et al., in "*Catalysis Communications*" (2003), Vol. 4, pp. 77-81, describe the selective dehydration of diols to allyl alcohols [i.e. 2-buten-1-ol (crotyl alcohol) and 3-buten-2-ol (methyl vinyl carbinol)] catalysed by cerium oxides obtained commercially or by dehydration of citrates. In particular, they describe selective dehydration catalysed by cerium oxide ($CeO_2$) of 1,3-butanediol to allyl alcohols (i.e. alkenols) at temperatures ranging from 300° C. to 375° C. In particular, 2-buten-1-ol (crotyl alcohol) and 3-buten-2-ol (methyl vinyl carbinol), are produced with high levels of selectivity in the dehydration of 1,3-butanediol catalysed by cerium oxide ($CeO_2$) operating at 325° C.

Sato S. et al., in "*Catalysis Communications*" (2004), Vol. 5, pp. 397-400, describe selective dehydration of 1,4-butanediol to 3-buten-1-ol (allyl carbinol) catalysed by cerium oxides operating at temperatures ranging from 200° C. to 450° C. Sato S. et al., in "*Applied Catalysis A: General*" (2007), Vol. 328, pp. 109-116, describe the vapour phase reaction of 1,3-butanediol catalysed by commercial rare earth oxides derived from the decomposition of the corresponding chlorides at temperatures >2000° C., for about 2 hours, in the vapour phase. During said reaction of 1,3-butanediol, either dehydration to unsaturated alcohols or the formation of by-products occur simultaneously at 325° C.

Gotoh H. et al., in "*Applied Catalysis A: General*" (2010), Vol. 377, pp. 92-98, describe the vapour phase dehydration of 1,3-butanediol catalysed by commercial rare earth oxides derived from the decomposition of the corresponding chlorides at elevated temperatures, and calcined at a different temperature (temperature ranging from 500° C. to 1000° C.) and thus having different crystalline structures.

Hichikawa N. et al., in "*Journal of Molecular Catalysis A: Chemical*" (2006), Vol. 256, pp. 106-112, describe the dehydration of 1,3-butanediol, in the presence of solids acidic catalysts such as, $SiO_2$—$Al_2O_3$, $Al_2O_3$, $ZrO_2$ and $TiO_2$, to unsaturated alcohols, as well as the dehydration of said unsaturated alcohols to 1,3-butadiene. For example, in the presence of $SiO_2$—$Al_2O_3$, good selectivity for unsaturated alcohols, in particular 3-buten-1-ol (allyl carbinol) and 2-buten-1-ol (crotyl alcohol) (see Table 2) is obtained, while operating at a temperature of 250° C., in the presence of $SiO_2$—$Al_2O_3$, alkenols, in particular 2-buten-1-ol (crotyl alcohol) and 3-buten-2-ol (methyl vinyl carbinol), are dehydrated to 1,3-butadiene (see Table 5).

The above-mentioned prior art merely describes the chemical mechanisms involved in diol dehydration reactions, in particular of 1,3-butanediol, to alkenols and from alkenols to 1,3-butadiene, but provides no indication of production processes for alkenols and 1,3-butadiene starting from diols derived from biosynthetic processes.

As for direct dehydration of diols to 1,3-butadiene, the only approaches which have found industrial application, albeit in specific contexts, are those based on Reppe type technologies which use phosphate-based catalysts.

For example, American U.S. Pat. No. 2,310,809 describes a process for the production of diolefins (for example, 1,3-butadiene) by dehydrating aliphatic glycols (for example, 1,4-butanediol, 1,3-butanediol), in the presence of phosphate-based catalysts, with 1,3-butadiene yields ranging from 85% to 95%. However, said process has proven difficult to apply because very low feed rates are used with consequent low catalyst productivity. Furthermore, recycle streams of organic substances such as, for example, benzene are used as "organic cleaners" in order to extend catalyst life.

Specifically because of the short life of the phosphate-based catalysts, American U.S. Pat. No. 2,426,678 describes a method for regenerating phosphate-based dehydration catalysts using volatile esters of phosphoric acid.

In recent years, new processes have been developed for synthesising diols, in particular 1,4-butanediol and 1,3-butanediol, starting from renewable sources. Said processes are based on the fermentation of sugars derived from renewable sources carried out in a fermentation broth, in the presence of at least one genetically modified microorganism for the purpose of producing 1,4-butanediol or 1,3-butanediol. Generally, said microorganism is genetically modified by introducing one or more exogenous genes which encode compounds belonging to the enzymatic pathway for producing 1,4-butanediol or 1,3-butanediol. Said microorganism may optionally also comprise gene disruption for the purpose of optimising the flow of carbon through the desired pathway for the production of 1,4-butanediol or 1,3-butanediol. Said renewable sources are, generally, biomass of vegetable origin: sugar cane and sugar beet may be used for this purpose as a source of sugars (sucrose), or maize and potato may be used as a source of starch and, hence, of dextrose. Of greater future interest are "non-food" biomasses such as, for example maize stalks, cereal straw, arundo, thistle stalks, guayule bagasse, etc., which may yield sugars by destructuration of the cellulose and hemicellulose. In general, biomass of vegetable origin is subjected to chemical and/or enzymatic hydrolysis in order to obtain substrates which may subsequently be processed biocatalytically in order to obtain the chemicals of interest. Said substrates include mixtures of carbohydrates, such as aromatic compounds and other products derived from the cellulose, hemicellulose and lignin present in the biomass. The carbohydrates obtained by hydrolysis of said biomass are a mixture rich in sugars with 5 and 6 carbon atoms which include, for example, sucrose, glucose, xylose, arabinose, galactose, mannose and fructose, which will be used during fermentation. Further details relating to the above-stated new processes for synthesising 1,4-butanediol starting from renewable sources may be found, for example, in American patent applications US 2009/0047719, US 2011/0003355; while for the synthesis of 1,3-butanediol they may be found, for example, in American patent applications US 2010/330635, US 2012/329113, US 2013/066035, US 2013/109064, which are incorporated herein by reference.

It is also known that, on completion of fermentation, the resultant fermentation broth also contains, in addition to the products of interest, i.e. 1,4-butanediol or 1,3-butanediol, a large quantity of water (for example, 90% by weight-95% by weight of water relative to total weight of the fermentation broth) as well as other impurities such as, for example:

inorganic salts (for example, sodium chloride, potassium chloride, calcium chloride, ammonium chloride, magnesium sulfate, ammonium sulfate; sodium, potassium or ammonium phosphates; sodium, potassium or ammonium citrates; sodium, potassium or ammonium acetates; sodium, potassium or ammonium borates); insoluble solid materials such as, for example, cellular debris, precipitated proteins. Said fermentation broth must thus be subjected to purification in order to obtain pure 1,4-butanediol or 1,3-butanediol with low water contents (i.e. water contents ranging from 1% by weight to 5% by weight of water relative to the total weight of the mixture obtained after purification).

In this connection, for example, the above-mentioned American patent application US 2011/0003355 describes a method for isolating 1,4-butanediol, it being emphasised that the method described therein may readily be modified for the purpose of isolating 1,3-butanediol. In a preferred aspect, a process is described for isolating 1,4-butanediol from the fermentation broth which includes removing a portion of solids by means of a disc stack centrifugation to obtain a liquid fraction; removing a further portion of solids from said liquid fraction by ultrafiltration; removing a portion of the salts from said liquid fraction by ion-exchange resins; evaporating a portion of the water and recovering the 1,4-butanediol by distillation.

However, the above-stated processes for isolating 1,4-butanediol or 1,3-butanediol from the fermentation broth, may have some problems. In particular, removing water by evaporation entails high energy consumption due to the heat required for removing substantially all the water (with the aim of ultimately having, as stated above, water contents ranging from 1% by weight to 5% by weight of water relative to the total weight of the mixture obtained after purification), and for separating the other impurities which are present, in particular for separating the impurities having a boiling point approximately the same as that of 1,4-butanediol or of 1,3-butanediol.

Furthermore, even after purification, the 1,4-butanediol and 1,3-butanediol may contain traces of inorganic salts and/or of organic compounds containing sulfur and/or nitrogen, which, as is known, are poisons for the catalysts normally used in subsequent processes for the use thereof, such as, for example, 1,3-butadiene production processes.

The Applicant has thus set itself the problem of finding a process for the production of 1,3-butadiene starting from a mixture comprising 1,3-butanediol and water, said water being present in a quantity of greater than or equal to 5% by weight relative to the total weight of said mixture, preferably from a mixture comprising 1,3-butanediol and water derived from the fermentation of sugars obtained from biomass, which process is capable of overcoming the above-described drawbacks.

The Applicant has now found that feeding a mixture comprising 1,3-butanediol and water to an evaporator makes it possible to use said mixture in a process for the production of 1,3-butadiene and to overcome the above-stated drawbacks. In particular, the Applicant has found a process for the production of 1,3-butadiene comprising feeding a mixture comprising 1,3-butanediol and water to an evaporator, said water being present in an amount of greater than or equal to 5% by weight relative to the total weight of said mixture; feeding the gaseous stream comprising 1,3-butanediol exiting from the top of said evaporator to a first reactor containing at least one dehydration catalyst; optionally feeding the stream comprising alkenols, water and, optionally, impurities and/or unreacted 1,3-butanediol, exiting from said first reactor to a purification section; feeding the, optionally purified, stream comprising alkenols, water and, optionally, impurities and/or unreacted 1,3-butanediol, to a second reactor containing at least one dehydration catalyst to obtain a stream comprising 1,3-butadiene, water and, optionally, impurities and/or unreacted alkenols; recovering the 1,3-butadiene from said stream. Preferably, said mixture comprising 1,3-butanediol and water is derived from the fermentation of sugars obtained from biomass.

Numerous advantages are obtained by the above-stated process. For example, said process surprisingly makes it possible to reduce energy consumption by at least 10% relative to a similar process using a feed of substantially pure 1,3-butanediol (i.e. with a purity of greater than or equal to 98%): this estimate was obtained using approaches known to a person skilled in the art (for example, by computer simulations combining, for example, Hysys and Excel software).

Furthermore, since the water present in said mixture acts as a thermal flywheel, said process may be carried out adiabatically so making it possible to use conventional fixed-bed reactors, into which the catalyst is charged, instead of tube bundle reactors. This permits simpler and less costly mechanical construction of the reactor.

Furthermore, said process, which takes advantage of the presence of water in said mixture, makes it possible to avoid having to remove substantially all of the water formed as a reaction product from the stream comprising alkenols, water and, optionally, impurities and/or unreacted 1,3-butanediol exiting from said first reactor, before said stream is fed to the second reactor for the production of 1,3-butadiene: this is advantageous because the alkenols and water form azeotropes which make it difficult and costly to remove the water from said stream (because water is generally separated from azeotropes by extractive distillation in the presence of solvents).

Furthermore, in the case in which a mixture comprising 1,3-butanediol and water derived from the fermentation of sugars obtained from biomass is used, said process permits capital cost savings of about 8%, because no purification section is required prior to the use thereof. Furthermore, the optional purification of the stream comprising alkenols, water and, optionally, impurities and/or unreacted 1,3-butanediol exiting from said first reactor is very much simpler than the purification of the mixture comprising 1,3-butanediol and water derived from the fermentation of sugars obtained from biomass because the impurities normally present therein, as stated above, have a boiling point approximately the same as that of 1,3-butanediol, but on the other hand have a boiling point which differs from that of the alkenols.

The present invention accordingly provides a process for the production of 1,3-butadiene comprising:
  feeding a mixture (a) comprising 1,3-butanediol and water to an evaporator, said water being present in an amount of greater than or equal to 5% by weight, preferably ranging from 10% by weight to 85% by weight, more preferably ranging from 15% by weight to 30% by weight, relative to the total weight of said mixture (a), to obtain:
    (b) a gaseous stream comprising 1,3-butanediol exiting from the top of said evaporator; and, optionally,
    (c) a blowdown stream exiting from the bottom of said evaporator;
  feeding said gaseous stream (b) to a first reactor containing at least one dehydration catalyst to obtain (d) a stream comprising alkenols, water and, optionally, impurities and/or unreacted 1,3-butanediol, exiting from said first reactor;

optionally, feeding said stream (d) to a first purification section to obtain:
(e) a stream comprising alkenols, water, and, optionally, impurities;
(f) a stream comprising water and, optionally, impurities and/or unreacted 1,3-butanediol; and, optionally,
(f') a stream comprising impurities;

feeding said stream (d) or said stream (e) to a second reactor containing at least one dehydration catalyst to obtain (g) a stream comprising 1,3-butadiene, water and, optionally, impurities and/or unreacted alkenols, exiting from said second reactor;

feeding said stream (g) to a second purification section to obtain:
(h) a stream comprising pure 1,3-butadiene;
(i) a stream comprising water and, optionally, unreacted alkenols; and, optionally,
(l) a stream comprising impurities.

According to a particularly preferred embodiment of the present invention, said mixture (a) is derived from the fermentation of sugars obtained from biomass.

For the aim of the present description and the following claims, unless stated otherwise, definitions of numerical ranges always include the extremes.

For the aim of the present description and the following claims, the term "comprising" also encompasses the terms "which essentially consists of" or "which consists of".

For the aim of the present description and the following claims, the term "biomass" denotes any organic material of vegetable origin including: products derived from agriculture such as, for example, guayule, thistle, maize, soy, cotton, flax seeds, rape seeds, sugar cane, palm oil, including discards, residues and waste derived from said products or from the processing thereof; products derived from crops specifically grown for energy use such as, for example, miscanthus, panic grass, giant cane, including discards, residues and waste derived from said products or from the processing thereof; products derived from forestry or silviculture products, including discards, residues and waste derived from said products or from the processing thereof; discards from agricultural products intended for human food or animal feedstuffs; residues from the paper industry; waste originating from separate collection of solid urban waste, such as, for example, urban waste of vegetable origin, paper.

According to one particularly preferred embodiment of the present invention, said mixture (a) is derived from the fermentation of sugars obtained from guayule or thistle, including discards, residues derived from said guayule and/or thistle or from the processing thereof. According to one still more preferred embodiment of the present invention, said mixture (a) is derived from the fermentation of sugars obtained from guayule, including discards, residues derived from said guayule or from the processing thereof.

The production of sugars from biomass may be performed by processes known in the art. For example, when biomass of vegetable origin (for example, lignocellulosic biomass) is used to produce sugars, said biomass is subjected to physical treatments (for example, extrusion, steam explosion, and the like), and/or to chemical and/or enzymatic hydrolysis, with mixtures of carbohydrates, aromatic compounds and other products derived from the cellulose, hemicellulose and lignin present in the biomass, being obtained. In particular, the resultant carbohydrates are mixtures of sugars with 5 and 6 carbon atoms which include, for example, sucrose, glucose, xylose, arabinose, galactose, mannose and fructose, which will be used in fermentation. Further details relating to processes for the production of sugars from biomass may be found, for example, in Italian patent application MI2013A002069 in the name of the present Applicant. Said fermentation is generally performed by microorganisms, in particular by genetically modified microorganisms, capable of producing the alcohols of interest. Further details relating to processes for synthesising 1,3-butanediol starting from renewable sources may be found, for example, in the above-stated American patent applications US 2010/330635, US 2012/329113, US 2013/066035, US 2013/109064.

In the case in which the mixture (a) is derived from the fermentation of sugars obtained from biomass, said mixture (a) may comprise impurities such as, for example: inorganic salts (for example, sodium chloride, potassium chloride, calcium chloride, ammonium chloride, magnesium sulfate, ammonium sulfate; sodium, potassium or ammonium phosphates; sodium, potassium or ammonium citrates; sodium, potassium or ammonium acetates; sodium, potassium or ammonium borates); insoluble solid materials such as, for example, cellular debris, precipitated proteins; unfermented sugars.

Any type of evaporator known in the art may advantageously be used for the aim of the present invention. Specific examples of evaporators which may advantageously be used are: "natural circulation" evaporators in which evaporation is brought about by motion induced solely by boiling, "kettle" type evaporators, evaporators in which evaporation is brought about by means of forced circulation in which velocity and turbulence are increased by using a circulation pump ("Forced-circulation Evaporators"), evaporators of the ME-EV ("Multi-Effect Evaporator") type, single or multiple stage evaporators, single effect evaporators, STV type evaporators ("Short Tube Vertical Evaporators"), LTV type evaporators ("Long Tube Vertical Evaporators"), "basket type" evaporators, horizontal tube evaporators, Falling Film Evaporators, thin-film evaporators ("Wiped Film Evaporators"), and the like. A "kettle" type evaporator is preferably used.

Further details relating to the types of evaporators used may be found, for example, in "Process Heat Transfer", Donald Q. Kern, McGraw-Hill (1950), Chapter 14, Evaporator, pp. 375-510; Perry's Chemical Engineers' Handbook, McGraw-Hill (7th Ed.—1997), Section 11, pp. 108-118.

According to a preferred embodiment of the present invention, said evaporator may operate at a temperature ranging from 95° C. to 300° C., preferably ranging from 130° C. to 280° C.

According to a preferred embodiment of the present invention, said evaporator may operate at a pressure ranging from 0.5 bara (bar absolute) to 5 bara (bar absolute), preferably ranging from 0.9 bara (bar absolute) to 3 bara (bar absolute).

It should be noted that, for the aim of the present invention, said mixture (a), before being fed to the evaporator, may be pre-heated in a heat exchanger (i.e. in the second heat exchanger as described below), by stream (d) which may be used entirely or in part for this purpose, thus permitting heat recovery. On exiting from said heat exchanger, stream (d) may be fed to said first purification section or to said second reactor.

It should furthermore be noted that, for the aim of the present invention, a small portion of the gaseous stream (b), once condensed, may be refluxed in the liquid phase to the top of said evaporator. Operating in this manner, the rising vapour and descending liquid are brought into contact in the dome of the evaporator which is equipped with a contact apparatus so as to avoid entraining high-boiling impurities which may contain substances which poison the catalyst. The remaining portion, on the other hand, is fed to said first reactor.

According to a preferred embodiment of the present invention, said blowdown stream (c) may exit from the evaporator at a flow rate such as to remove a quantity of mixture (a) fed to said evaporator ranging from 0.5% by weight to 5% by weight, preferably ranging from 1% by weight to 4% by weight, relative to the total weight of said mixture (a) fed to the evaporator in one hour.

It should be noted that said blowdown stream is particularly useful in the case in which mixture (a) is derived from the fermentation of sugars obtained from biomass: in this case, as has been stated above, said mixture (a) may comprise impurities which may be eliminated in this manner (entirely or at least in part).

According to a preferred embodiment of the present invention, the catalyst contained in said first reactor may be selected from among acidic catalysts such as, for example, cerium oxide ($CeO_2$), aluminium oxide ($\gamma$-$Al_2O_3$), aluminium silicate ($SiO_2$—$Al_2O_3$), sulfonated resins, ion-exchange resins, acidic earths (for example lanthanum oxide or zirconium oxide). Said catalysts may optionally be supported on inert carriers such as, for example, pumice, graphite, silica. Cerium oxide ($CeO_2$) is preferred.

According to a preferred embodiment of the present invention, said first reactor may operate at a temperature ranging from 190° C. to 450° C., preferably ranging from 320° C. to 420° C.

According to a preferred embodiment of the present invention, said first reactor may operate at a pressure ranging from 0.3 bara (bar absolute) to 2 bara (bar absolute), preferably ranging from 0.8 bara (bar absolute) to 1.8 bara (bar absolute).

According to a preferred embodiment of the present invention, the gaseous stream (b) may be fed to said first reactor operating at a "Weight Hourly Space Velocity" (WHSV), i.e. at a ratio between the weight of the gas stream (b) fed in one hour and the weight of catalyst, said ratio being measured in $h^{-1}$, ranging from 0.5 $h^{-1}$ and 30 $h^{-1}$, preferably ranging from 1 $h^{-1}$ and 20 $h^{-1}$, more preferably ranging from 2 $h^{-1}$ to 15 $h^{-1}$.

Preferably, the gaseous stream (b) exiting from the top of the evaporator may be pre-heated in a first heat exchanger by stream (d) which may be used entirely or in part for this purpose, thus permitting a first heat recovery. On exiting from said first heat exchanger, stream (d) may be fed, entirely or in part, to a second heat exchanger for the purpose, as stated above, of pre-heating mixture (a) before it is fed to the evaporator, thus permitting a second heat recovery. On exiting from said second heat exchanger, stream (d) may be fed to said first purification section or to said second reactor. Said pre-heated gaseous stream (b) may be fed to a third heat exchanger so as to achieve the input temperature into said first reactor, said temperature being ranging from 190° C. to 450° C., preferably ranging from 320° C. to 420° C.

It should be noted that, with the aim of avoiding catalyst fluidisation phenomena, said first reactor is preferably fed with a downflow configuration.

A gaseous stream (d) exits from said first reactor, said stream comprising alkenols, i.e. 2-buten-1-ol (crotyl alcohol), 3-buten-2-ol (methyl vinyl carbinol), 3-buten-1-ol (allyl carbinol), more particularly 2-buten-1-ol (crotyl alcohol) and 3-buten-2-ol (methyl vinyl carbinol), water and, optionally, impurities and/or unreacted 1,3-butanediol. In general, assuming 1,3-butanediol conversion to be greater than or equal to 90%, preferably equal to 100%, said stream (d) comprises: alkenols in a quantity of greater than or equal to 50% by weight, water in a quantity of greater than or equal to 20% by weight, unreacted 1,3-butanediol and optional impurities in a quantity of less than or equal to 15% by weight, said quantity being expressed in % by weight relative to the total weight of said stream (d). Preferably, said first purification section may comprise two distillation columns. Preferably, stream (d) exiting from said first reactor, after optional heat recovery in the above-stated first and/or second heat exchangers, may be fed to a first distillation column to obtain a stream (f') exiting from the top of said first distillation column comprising light impurities (for example, acetaldehyde, butenes) and a stream exiting from the bottom of said first distillation column which is fed to a second distillation column. A gaseous stream (e) exits from the top of said second distillation column, said stream comprising alkenols, water and, optionally, impurities, while a stream (f) exits from the bottom of said distillation column, said stream comprising water and, optionally, heavy impurities (for example, alkenol oligomers, oxygenated butene dimers, unsaturated acids having 8 carbon atoms) and/or unreacted 1,3-butanediol, said unreacted 1,3-butanediol generally being present in a quantity of less than or equal to 98% by weight relative to the total weight of said stream (f) which is preferably fed to said evaporator. Generally, said stream (e) comprises: alkenols in a quantity of greater than or equal to 45% by weight, water in a quantity of greater than or equal to 30% by weight, and optional impurities (for example, 2-butanone, heptanone, acetaldehyde, hydrocarbons having two, three or four carbon atoms) in a quantity of less than or equal to 15% by weight, preferably of less than or equal to 10% by weight, relative to the total weight of said stream (e).

According to a preferred embodiment of the present invention, the catalyst present in said second reactor may be selected from among acidic catalysts such as, for example, aluminium oxide ($\gamma$—$Al_2O_3$), aluminium silicate ($SiO_2$—$Al_2O_3$), aluminas, zeolites, sulfonated resins, ion-exchange resins, metal phosphates (for example, boron phosphate, aluminium phosphate, calcium phosphate, sodium phosphate, cerium phosphate), ammonium phosphate, acidic earths (for example, lanthanum oxide, zirconium oxide). Said catalysts may optionally be supported on inert carriers such as, for example, pumice, graphite, silica. Aluminium silicate ($SiO_2$—$Al_2O_3$), metal phosphates (preferably, calcium phosphate), are preferred.

For the aim of the present invention and the following claims, the term "zeolites" is taken to have its widest meaning, i.e. also comprising those materials conventionally known, for example, as "zeolite-like", "zeotype", and the like.

According to a preferred embodiment of the present invention, said second reactor may operate at a temperature ranging from 250° C. to 450° C., preferably ranging from 280° C. to 400° C.

According to a preferred embodiment of the present invention, said second reactor may operate at a pressure ranging from 0.3 bara (bar absolute) to 2 bara (bar absolute), preferably ranging from 0.8 bara (bar absolute) to 1.8 bara (bar absolute). According to a preferred embodiment of the present invention, said stream (d) or said stream (e) may be fed to said second reactor operating at a "Weight Hourly Space Velocity" (WHSV), i.e. at a ratio between the weight of said stream (d) or of said stream (e) fed in one hour and the weight of catalyst, said ratio being measured in $h^{-1}$, ranging from $0.5\ h^{-1}$ to $20\ h^-$, preferably ranging from $1\ h^{-1}$ to $10\ h^{-1}$.

Preferably, said stream (d) or said stream (e) may be pre-heated in a third heat exchanger, so providing a third heat recovery. On exiting from said third heat exchanger, said stream (d) or said pre-heated stream (e) may be fed to a fourth heat exchanger so as to achieve the input temperature into said second reactor ranging from 250° C. to 450° C., preferably ranging from 280° C. to 400° C.

It should be noted that, with the aim of avoiding catalyst fluidisation phenomena, said second reactor is preferably fed with a downflow configuration.

Stream (g) is fed to a second purification section in order to obtain a stream (h) comprising pure 1,3-butadiene (purity ≥90%, preferably ≥99%), a stream (i) comprising water and, optionally, unreacted alkenols, said unreacted alkenols generally being present in a quantity of less than or equal to 30% by weight relative to the total weight of said stream (i), and, optionally, a stream (I) comprising impurities (for example, aldehydes, ketones having 4 carbon atoms, or compounds derived from the condensation thereof). Said second purification section may comprise one or more distillation columns.

For the aim of the present invention, said process for the production of 1,3-butadiene is preferably carried out continuously. Said first reactor and said second reactor may be fixed-bed, or fluidised-bed, preferably fixed-bed. Said first reactor and said second reactor may be adiabatic, isothermal or a combination of the two, preferably adiabatic.

As stated above, said 1,3-butadiene may advantageously be used as a monomer or as an intermediate in the production of elastomers and (co)polymers.

Furthermore, as stated above, the alkenols obtained from the above-stated process, i.e. from the dehydration of 1,3-butanediol in the first reactor, namely 2-buten-1-ol (crotyl alcohol), 3-buten-2-ol (methyl vinyl carbinol), 3-buten-1-ol (allyl carbinol), more particularly 2-buten-1-ol (crotyl alcohol) and 3-buten-2-ol (methyl vinyl carbinol), may advantageously also be used, other than for the production of 1,3-butadiene, in the production of intermediates which are in turn usable in fine chemistry, agricultural chemistry, pharmaceutical chemistry, or in petrochemistry.

It should be noted that, in the case in which a mixture is present which comprises at least one of the above-stated alkenols, said mixture being derived from the fermentation of sugars obtained from biomass, said mixture may be fed directly to said evaporator and, subsequently, to said second reactor.

The present invention accordingly further provides a process for the production of 1,3-butadiene comprising feeding a mixture comprising at least one of the above-stated alkenols, said mixture being derived from the fermentation of sugars obtained from biomass, to said evaporator and, subsequently to said second reactor. The operating conditions for said evaporator and said second reactor are same as those mentioned above.

The present invention will now be illustrated in greater detail by an embodiment with reference to FIG. 1 shown below.

The process provided by the present invention may be carried out as shown, for example, in FIG. 1.

In this connection, a mixture (a) comprising 1,3-butanediol and water, said mixture (a) preferably being derived from the fermentation of sugars obtained from biomass, is fed to an evaporator (A) to obtain a gaseous stream (b) comprising 1,3-butanediol exiting from the top of said evaporator (A) and a blowdown stream (c) exiting from the bottom of said evaporator (A). Said gaseous stream (b) is fed to a first reactor (B) containing at least one dehydration catalyst to obtain a stream (d) comprising alkenols, water and, optionally, impurities and/or unreacted 1,3-butanediol, exiting from said first reactor (B). Said stream (d) is fed to a first purification section (C) to obtain a stream (e) comprising alkenols, water and, optionally, impurities, a stream (f) comprising water and, optionally, impurities and/or unreacted 1,3-butanediol which is fed to said evaporator (A), and a stream (f') comprising impurities. Said stream (e) is fed to a second reactor (D) containing at least one dehydration catalyst to obtain a stream (g) comprising 1,3-butadiene, water and, optionally, impurities and/or unreacted alkenols, exiting from said second reactor (D). Said stream (g) is fed to a second purification section (E) to obtain a stream (h) comprising pure 1,3-butadiene, a stream (i) comprising water and, optionally, unreacted alkenols which is fed to said first purification section (C), and a stream (I) comprising impurities. Some illustrative, non-limiting examples of the present invention are provided below to assist in understanding the present invention and the implementation thereof.

EXAMPLE 1

The description of the present example makes reference to FIG. 1 shown below. Table 2 shows the results obtained in terms of conversion (C %), selectivity (S %) and yield (Y %), expressed by calculating the conversion of 1,3-butanediol (1,3-BDO) ($C_{1,3\text{-}BDO}$), selectivity for alkenols ($S_i$) and yield of alkenols ($Y_{ALK}$) alkenol (ALK.) conversion ($C_{ALK}$), selectivity for 1,3-butadiene (1,3-BDE) ($S_{1,3\text{-}BDE}$) and yield of 1,3-butadiene (1,3-BDE) ($Y_{1,3\text{-}BDE}$), according to the formulae shown below.

$$C_{1,3-BDO} = \frac{(moles_{1,3-BDO})_{in} - (moles_{1,3-BDO})_{out}}{(moles_{1,3-BDO})_{in}} \times 100;$$

$$S_i = \frac{moles_{ALK.}}{(moles_{1,3-BDO})_{in} - (moles_{1,3-BDO})_{out}} \times 100;$$

$$C_{ALK.} = \frac{(moles_{ALK.})_{in} - (moles_{ALK.})_{out}}{(moles_{ALK.})_{in}} \times 100;$$

$$S_{1,3-BDE} = \frac{moles_{1,3-BDE}}{(moles_{ALK.})_{in} - (moles_{ALK.})_{out}} \times 100;$$

$$Y_{ALK.} = \frac{C_{1,3BDO} \times S_i}{100};$$

$$Y_{1,3-BDE} = \frac{C_{ALK.} \times S_{1,3-BDE}}{100}$$

in which:

$(moles_{1,3-BDO})_{in}$ = input moles of 1, 3 – butanediol;

$(moles_{1,3-BDO})_{out}$ = output moles of 1, 3 – butanediol;

$moles_{ALK.}$ = total moles of alkenols [based on 3-buten-2-ol (methyl vinyl carbinol) and 2-buten-1-ol (crotyl alcohol)];

$(moles_{ALK.})_{in}$ = input moles of alkenols;

$(moles_{ALK.})_{out}$ = output moles of alkenols;

$moles_{1,3-BDE}$ = total moles of 1, 3-butadiene.

Table 3 shows the characterisation of the streams obtained, in which the weight percentages of the compound (s) are expressed relative to the total weight of the stream obtained, characterisation being carried out as described below.

(i) Preparation of Alkenols from a Mixture of 1,3-Butanediol

A mixture (a) comprising 1,3-butanediol and water having the following composition was used for this purpose: 17% by weight of water relative to the total weight of said mixture comprising 1,3-butanediol.

A first tubular reactor, with an internal diameter of 10 mm, was charged with 10 g of cerium oxide ($CeO_2$ pellets of about 1 mm). Said first tubular reactor was heated with an electrical oven and the temperature inside the reactor was maintained at 400° C. during the test. The temperature of the evaporator was maintained at 250° C. during the test. The pressure inside said first tubular reactor and the evaporator was maintained at atmospheric pressure (1 bara). The outlet from said first reactor was connected to a first condenser operating at 15° C. in order to recover those products which are liquid at room temperature. The vent of the flask for collecting the condensed liquid was connected to a sampling system made up of a steel cylinder of a volume of 300 ml equipped with intercept valves at each of the two ends. The gas flowed through the steel cylinder and the outlet from the latter was connected to a volumetric meter which measured the quantity of gas which evolved.

The above-stated mixture (a) comprising 1,3-butanediol and water was fed to said evaporator operating under the above-stated conditions at a flow rate of 100 g/h, vaporised, and fed to said first reactor at a WHSV of 10 $h^{-1}$, said first reactor operating under the above-stated conditions. On exiting from said first reactor, the stream (d) obtained, the composition of which is shown in Table 3, was condensed, weighed and analysed by gas chromatography. The gas which evolved was measured and likewise analysed by gas chromatography. Table 2 shows the obtained results.

(ii) Purification of [Stream (d)]

Stream (d) obtained as described above was subjected to a first purification by distillation for the purpose of removing unreacted 1,3-butanediol. It should be noted that the alkenols present in said stream (d) form azeotropic mixtures with water, for which reason they cannot be separated from water by simple distillation in such a manner as to obtain them in pure form.

Distillation was carried out at atmospheric pressure, adding 3,5-di-tert-4-butylhydroxytoluene (BHT) to said stream (d) present in a boiler so as to obtain a concentration of the same of about 200 ppm in said stream (d). Said distillation was carried out using a 40-tray Oldershaw column (2×20 tray sections), by charging said stream (d) into the boiler in a single portion and taking various top cuts on the basis of the recorded temperatures, so gradually concentrating the heavier components in the boiler. The distillation conditions (reflux ratio, boiler heating power, quantity of distillate taken) were varied as a function of the boiling temperatures of the species to be separated and the recorded top temperatures.

Table 1 shows the distillation conditions.

TABLE 1

Alkenol distillation conditions at atmospheric pressure

| | ΔT boiler (° C.) | ΔT top (° C.) | RR[1] | [H$_2$O] (% wt./ wt.)[2] | Density (g/cm$^3$) |
|---|---|---|---|---|---|
| Charge | — | — | — | 11.8 | — |
| Fraction 1 | 101.3-103.0 | 56.0-84.5 | 100 | 11.3 | 0.84 |
| Fraction 2 | 103.1-104.3 | 85.0-86.8 | 100-30 | 24.1 | 0.87 |
| Fraction 3 | 104.9-113.6 | 86.4-87.1 | 30 | 25.2 | 0.87 |
| Fraction 4 | 114.6-152.3 | 87.1-94.4 | 30-40 | 34.4 | 0.89 |
| Fraction 5 | 154.3-167.9 | 93.6-119.4 | 40-60 | 31.3 | 0.90 |
| Fraction 6 | 169.2-208.6 | 120.1-121.2 | 60-70 | 1.03 | 0.85 |
| Fraction 7 | 208.6-210.8 | 121.2-130.1 | 70 | 1.35 | 0.85 |
| Boiler | — | — | — | 0.029 | — |

[1]reflux ratio;
[2]% by weight of water relative to total weight of the fraction.

In particular:

Fraction 1 (up to about 84° C.) corresponds to the light cut to be removed;

Fraction 2 and Fraction 3 correspond to an azeotrope at T=86.5° C.-87° C. between the lowest-boiling alkenol, i.e. 3-buten-2-ol (methyl vinyl carbinol) and water (said azeotrope having the composition: 73% by weight 3-buten-2-ol: 25% by weight water);

2-buten-1-ol (crotyl alcohol in cis and trans forms) and a small proportion of 3-buten-1-ol (allyl carbinol) together with 35% by weight of water start to distil off in Fraction 4;

water is exhausted in Fraction 5 and the temperature thus rises to about 120° C.;

Fraction 6 and Fraction 7 correspond to 95%-97% 2-buten-1-ol (crotyl alcohol). The above-stated distillation yields a stream (e), the composition of which is shown in Table 3 and which is fed to a second reactor operating as stated below.

(iii) Preparation of 1,3 Butadiene from Stream (e)

A second reactor was used for this purpose. Said second reactor had the same characteristics as the above-described first reactor in stage (i) but was charged with 3 grams of aluminium silicate ($SiO_2$—$Al_2O_3$). Stream (e) was fed, in vapour form, at a WHSV of 3.3 $h^{-1}$ to said second reactor operating at atmospheric pressure (1 bara) and at a temperature of 300° C. On exiting from said second reactor, the stream (g) obtained, the composition of which is shown in Table 3, was condensed, weighed and analysed by gas chromatography. The gas which evolved was measured and likewise analysed by gas chromatography. Table 2 shows the obtained results.

TABLE 2

| 1st DEHYDRATION REACTOR | | |
|---|---|---|
| 1,3-BDO conversion | % mol | 94% |
| Selectivity for alkenols[1] | % mol | 85% |
| Yield of alkenols[1] | % mol | 80% |
| 2nd DEHYDRATION REACTOR | | |
| Alkenol conversion[1] | % mol | 99% |
| Selectivity for 1,3-BDE | % mol | 89% |
| 1,3-BDE yield | % mol | 88% |

[1]based on 3-buten-2-ol (methyl vinyl carbinol) and 2-buten-1-ol (crotyl alcohol).

TABLE 3

| COMPOUNDS | STREAM | | | | |
|---|---|---|---|---|---|
| | (a) | (d) | (e) | (g) | (h) |
| 1,3-Butadiene | 0.0% | 0.0% | 0.0% | 45.2% | 99.8% |
| 1,3-Butanediol | 83.0% | 4.9% | 0.0% | 0.0% | 0.0% |
| Water | 17.0% | 30.6% | 39.2% | 49.4% | 0.0% |
| Light compounds[(2)] | 0.0% | 7.5% | 0.1% | 2.3% | 0.2% |
| Alkenols | 0.0% | 53.3% | 59.1% | 0.0% | 0.0% |
| Medium-boiling compounds[(3)] | 0.0% | 2.3% | 1.5% | 1.2% | 0.0% |
| Heavy compounds[(4)] | 0.0% | 1.4% | 0.1% | 1.9% | 0.0% |

[(2)]compounds lighter than the low-boiling alkenol, i.e. 3-buten-2-ol (methyl vinyl carbinol) ($T_{BOILING}$ = 97° C.), excluding 1,3-butadiene;
[(3)]compounds lighter than the high-boiling alkenol, i.e. 2-buten-1-ol (crotyl alcohol) ($T_{BOILING}$ = 121.5° C.); heavier than the low-boiling alkenol, i.e. 3-buten-2-ol (methyl vinyl carbinol) ($T_{BOILING}$ = 97° C.), excluding 1,3-butadiene [includes the medium-boiling alkenol 3-buten-1-ol (allyl carbinol) ($T_{BOILING}$ = 113.5)];
[(4)]compounds heavier than the high-boiling alkenol, i.e. 2-buten-1-ol (crotyl alcohol) ($T_{BOILING}$ = 121.5° C.).

The invention claimed is:

1. Process for the production of 1,3-butadiene comprising:
   feeding a mixture comprising 1,3-butanediol and water to an evaporator, said water being present in an amount of greater than or equal to 5% by weight, relative to the total weight of said mixture, to obtain:
     a gaseous stream comprising 1,3-butanediol exiting from the top of said evaporator;
   feeding said gaseous stream to a first reactor containing at least one first dehydration catalyst to obtain an alkenol stream comprising alkenols and water, exiting from said first reactor;
   feeding said alkenol stream to a second reactor containing at least one second dehydration catalyst to obtain a butadiene stream comprising 1,3-butadiene and water exiting from said second reactor;
     feeding said butadiene stream to a second purification section to obtain:
     a stream comprising pure 1,3-butadiene; and
     a stream comprising water.

2. Process for the production of 1,3-butadiene according to claim 1, in which said mixture is derived from the fermentation of sugars obtained from biomass.

3. Process for the production of 1,3-butadiene according to claim 1, in which said mixture is derived from the fermentation of sugars obtained from at least one of guayule and thistle, including discards, residues derived from the at least one of guayule and thistle or from processing thereof.

4. Process for the production of 1,3-butadiene according to claim 1, in which said evaporator operates according to at least one of the following:
   at a temperature ranging from 95° C. to 300° C.; and
   at a pressure ranging from 0.5 bar absolute to 5 bar absolute.

5. Process for the production of 1,3-butadiene according to claim 1, wherein the step of feeding said mixture to said evaporator is carried out to obtain:
   said gaseous stream exiting from the top of said evaporator; and
   a blowdown stream exiting from a bottom of said evaporator;
   in which said blowdown stream exits from said evaporator at a flow rate such as to remove a quantity of said mixture fed to said evaporator ranging from 0.5% by weight to 5% by weight, relative to a total weight of said mixture fed to said evaporator in one hour.

6. Process for the production of 1,3-butadiene according to claim 1, in which the at least one first catalyst contained in said first reactor is selected from cerium oxide ($CeO_2$), aluminium oxide ($\gamma$-$Al_2O_3$), aluminium silicate ($SiO_2$—$Al_2O_3$), sulfonated resins, ion-exchange resins, and acidic earths, the at least one first catalyst optionally being supported on an inert carrier.

7. Process for the production of 1,3-butadiene according to claim 1, in which said first reactor operates according to at least one of the following:
   at a temperature ranging from 190° C. to 450° C.; and
   at a pressure ranging from 0.3 bar absolute to 2 bar absolute.

8. Process for the production of 1,3-butadiene according to claim 1, in which said gaseous stream is fed to said first reactor operating at a "Weight Hourly Space Velocity", which is at a ratio between a weight of said gaseous stream fed in one hour and a weight of the at least one first catalyst, said ratio being measured in $h^{-1}$, ranging from 0.5 $h^{-1}$ to 30 $h^{-1}$.

9. Process for the production of 1,3-butadiene according to claim 1, in which the at least one second catalyst contained in said second reactor is selected from aluminium oxide ($\gamma$-$Al_2O_3$), aluminium silicate ($SiO_2$—$Al_2O_3$), aluminas, zeolites, sulfonated resins, ion-exchange resins, metal phosphates, ammonium phosphate, and acidic earths, the at least one second catalyst optionally being supported on an inert carrier.

10. Process for the production of 1,3-butadiene according to claim 1, in which said second reactor operates according to at least one of the following:
    at a temperature ranging from 250° C. to 450° C.; and
    at a pressure ranging from 0.3 bar absolute to 2 bar absolute.

11. Process for the production of 1,3-butadiene according to claim 1, wherein said alkenol stream is fed to a first purification section to obtain:
    (i) a stream comprising alkenols, water, and optional impurities;
    (ii) a stream comprising water and optionally at least one of impurities and unreacted 1,3-butanediol; and,
    (ii) an optional stream comprising impurities;
    in which said alkenol stream or said stream (i) is fed to said second reactor operating at a "Weight Hourly Space Velocity", which is at a ratio between a weight of said alkenol stream or of said stream (i) fed in one hour and the weight of catalyst, said ratio being measured in $h^{-1}$, ranging from 0.5 $h^{-1}$ to 20 $h^{-1}$.

12. Process for the production of 1,3-butadiene according to claim 1 wherein said mixture is derived from biomass, said biomass derived mixture comprising at least one alkenol selected from 2-buten-1-ol, 3-buten-2-ol, and 3-buten-1-ol, said biomass derived mixture being derived from the fermentation of sugars obtained from biomass.

13. Process for the production of 1,3-butadiene according to claim 1 wherein said gaseous stream is fed to said first reactor containing the at least one first dehydration catalyst to obtain said alkenol stream comprising said alkenols, said water and at least one of impurities and unreacted 1,3-butanediol, exiting from said first reactor.

14. Process for the production of 1,3-butadiene according to claim 1 wherein said alkenol stream is fed to a first purification section to obtain:
    (i) a stream comprising alkenols, water, and optional impurities;
    (ii) a stream comprising water and optionally at least one of impurities and unreacted 1,3-butanediol; and,
    (ii') an optional stream comprising impurities.

15. Process for the production of 1,3-butadiene according to claim 14 wherein said alkenol stream or said stream (i) is fed to said second reactor to obtain said butadiene stream comprising said 1,3-butadiene, said water and at least one of impurities and unreacted alkenols, exiting from said second reactor.

16. Process for the production of 1,3-butadiene according to claim 1 wherein the step of feeding said butadiene stream to said second purification section obtains:
a stream comprising pure 1,3-butadiene;
a stream comprising water and optional unreacted alkenols; and,
an optional stream comprising impurities.

17. Process for the production of 1,3-butadiene according to claim 1 wherein said water is present in said mixture an amount ranging from 10% by weight to 85% by weight relative to a total weight of said mixture.

18. Process for the production of 1,3-butadiene according to claim 1 wherein said water is present in said mixture an amount ranging from 15% by weight to 30% by weight relative to a total weight of said mixture.

19. Process for the production of 1,3-butadiene comprising:
feeding a mixture (a) comprising 1,3-butanediol and water to an evaporator, said water being present in an amount of greater than or equal to 5% by weight relative to the total weight of said mixture (a), to obtain:
(b) a gaseous stream comprising 1,3-butanediol exiting from the top of said evaporator; and
(c) an optional blowdown stream exiting from a bottom of said evaporator;
feeding said gaseous stream (b) to a first reactor containing at least one first dehydration catalyst to obtain an alkenol stream (d) comprising alkenols, water and, optionally, at least one of impurities and unreacted 1,3-butanediol, exiting from said first reactor;
feeding said alkenol stream (d) to a first purification section to obtain:
(e) a stream comprising alkenols, water, and optional impurities;
(f) a stream comprising water and optionally at least one of impurities and unreacted 1,3-butanediol; and,
(f') an optional stream comprising impurities;
feeding said alkenol stream (d) or said stream (e) to a second reactor containing at least one second dehydration catalyst to obtain a butadiene stream (g) comprising 1,3-butadiene, water and optionally at least one of impurities and unreacted alkenols, exiting from said second reactor;
feeding said butadiene stream (g) to a second purification section to obtain:
(h) a stream comprising pure 1,3-butadiene;
(i) a stream comprising water and optional unreacted alkenols; and,
(l) an optional stream comprising impurities.

20. Process for the production of 1,3-butadiene according to claim 19, in which said evaporator operates according to at least one of the following:
at a temperature ranging from 95° C. to 300° C.; and
at a pressure ranging from 0.5 bar absolute to 5 bar absolute.

21. Process for the production of 1,3-butadiene according to claim 20, in which said first reactor operates according to at least one of the following:
at a temperature ranging from 190° C. to 450° C.; and
at a pressure ranging from 0.3 bar absolute to 2 bar absolute.

22. Process for the production of 1,3-butadiene according to claim 21 in which said gaseous stream (b) is fed to said first reactor operating at a "Weight Hourly Space Velocity", which is at a ratio between a weight of said gaseous stream (b) fed in one hour and a weight of the at least one first catalyst, said ratio being measured in $h^{-1}$, ranging from 0.5 $h^{-1}$ to 30 $h^{-1}$.

23. Process for the production of 1,3-butadiene according to claim 22, in which said second reactor operates according to at least one of the following:
at a temperature ranging from 250° C. to 450° C.; and
at a pressure ranging from 0.3 bar absolute to 2 bar absolute.

24. Process for the production of 1,3-butadiene according to claim 23, wherein said alkenol stream (d) or said stream (e) is fed to said second reactor operating at a "Weight Hourly Space Velocity", which is at a ratio between a weight of said alkenol stream (d) or of said stream (e) fed in one hour and the weight of catalyst, said ratio being measured in $h^{-1}$, ranging from 0.5 $h^{-1}$ to 20 $h^{-1}$.

25. Process for the production of 1,3-butadiene according to claim 19 wherein said water is present in said mixture (a) in an amount ranging from 15% by weight to 30% by weight relative to a total weight of said mixture (a).

26. Process for the production of 1,3-butadiene according to claim 19 wherein said mixture (a) is derived from biomass, said biomass derived mixture comprising at least one alkenol selected from 2-buten-1-ol, 3-buten-2-ol, and 3-buten-1-ol, said biomass derived mixture being derived from the fermentation of sugars obtained from biomass.

\* \* \* \* \*